(12) United States Patent  
Childs

(10) Patent No.: US 8,636,655 B1  
(45) Date of Patent: Jan. 28, 2014

(54) TISSUE RETRACTION SYSTEM AND RELATED METHODS

(76) Inventor: Ronald Childs, Fairfax, VA (US)

(\*) Notice: Subject to any disclaimer, the term of this patent is extended or adjusted under 35 U.S.C. 154(b) by 211 days.

(21) Appl. No.: 13/009,829

(22) Filed: Jan. 19, 2011

Related U.S. Application Data

(60) Provisional application No. 61/296,468, filed on Jan. 19, 2010.

(51) Int. Cl.  
*A61B 1/32* (2006.01)

(52) U.S. Cl.  
USPC .......................................................... 600/219

(58) Field of Classification Search  
USPC ............... 606/86 A, 86 B, 99, 104, 105, 279; 600/203, 210, 214, 216, 219, 235  
See application file for complete search history.

(56) References Cited

U.S. PATENT DOCUMENTS

| | | |
|---|---|---|
| 186,637 A | 1/1877 | Tanner |
| 1,223,812 A | 4/1917 | Listiak |
| 1,456,116 A | 5/1923 | Bessesen |
| 1,520,832 A | 12/1924 | McConnell |
| 2,807,259 A | 9/1957 | Guerriero |
| 3,030,948 A | 4/1962 | Loeffler |
| 3,364,919 A | 1/1968 | Hunnicutt |
| 3,383,769 A | 5/1968 | Davis |
| 3,384,077 A | 5/1968 | Gauthier |
| 3,509,873 A | 5/1970 | Karlin et al. |
| 3,522,799 A | 8/1970 | Gauthier |
| 3,724,449 A | 4/1973 | Gauthier |
| 3,749,088 A | 7/1973 | Kolhmann |
| 3,795,981 A | 3/1974 | Franklin et al. |
| 3,965,890 A | 6/1976 | Gauthier |
| 4,116,232 A | 9/1978 | Rabban |
| 4,156,424 A | 5/1979 | Burgin |
| 4,165,746 A | 8/1979 | Burgin |
| 4,566,466 A | 1/1986 | Ripple et al. |
| 4,686,972 A | 8/1987 | Kurland |
| 4,702,230 A | 10/1987 | Pelta |
| 4,747,394 A | 5/1988 | Watanabe |
| 4,747,395 A | 5/1988 | Brief |
| 4,817,587 A | 4/1989 | Janese |
| 4,829,985 A | 5/1989 | Couetil |
| 4,852,552 A | 8/1989 | Chaux |
| 4,877,020 A | 10/1989 | Vich |
| 4,881,525 A | 11/1989 | Williams |

(Continued)

FOREIGN PATENT DOCUMENTS

| | | |
|---|---|---|
| CN | 201341901 | 11/2009 |
| CN | 201537102 | 8/2010 |

(Continued)

OTHER PUBLICATIONS

Deutsch and Musacchio, "Minimally invasive transforaminal lumbar interbody fusion with unilateral pedicle screw fixation," *Neurosurg Focus*, 2006 20(3): E10, 5 pages.

(Continued)

*Primary Examiner* — Mary Hoffman  
*Assistant Examiner* — Tara Carter  
(74) *Attorney, Agent, or Firm* — Jonathan Spangler; Rory Schermerhorn

(57) ABSTRACT

Instruments, and methods for performing surgical procedures on the spine, including creating an operative corridor to the spine with a tissue retraction system and registering the tissue retraction system to the patient.

7 Claims, 8 Drawing Sheets

(56) References Cited

U.S. PATENT DOCUMENTS

| | | |
|---|---|---|
| 4,934,352 A | 6/1990 | Sullivan |
| 5,052,373 A | 10/1991 | Michelson |
| 5,339,801 A | 8/1994 | Poloyko |
| 5,400,774 A | 3/1995 | Villalta et al. |
| 5,417,230 A | 5/1995 | Wood |
| 5,431,658 A | 7/1995 | Moskovich |
| 5,512,038 A | 4/1996 | O'Neal |
| 5,609,593 A | 3/1997 | Errico et al. |
| 5,728,046 A | 3/1998 | Mayer et al. |
| 5,733,290 A | 3/1998 | McCue |
| 5,746,743 A | 5/1998 | Greenberg |
| 5,755,660 A | 5/1998 | Tyagi |
| 5,755,732 A | 5/1998 | Green et al. |
| 5,772,583 A | 6/1998 | Wright |
| 5,782,830 A | 7/1998 | Farris |
| 5,795,291 A | 8/1998 | Koros et al. |
| 5,797,909 A | 8/1998 | Michelson |
| 5,846,192 A | 12/1998 | Teixido |
| 5,882,298 A | 3/1999 | Sharratt |
| 5,890,271 A | 4/1999 | Bromley |
| 5,893,831 A | 4/1999 | Koros et al. |
| 5,902,233 A | 5/1999 | Farley |
| 5,928,139 A | 7/1999 | Koros et al. |
| 5,931,777 A | 8/1999 | Sava |
| 5,944,658 A | 8/1999 | Koros |
| 5,967,972 A | 10/1999 | Santilli |
| 5,984,865 A | 11/1999 | Farley |
| 5,993,385 A | 11/1999 | Johnston |
| 6,042,540 A | 3/2000 | Johnston |
| 6,042,542 A | 3/2000 | Koros |
| 6,096,038 A | 8/2000 | Michelson |
| 6,132,370 A | 10/2000 | Furnish |
| 6,139,493 A | 10/2000 | Koros |
| 6,159,215 A | 12/2000 | Urbahns et al. |
| 6,206,826 B1 | 3/2001 | Mathews |
| 6,224,545 B1 | 5/2001 | Cocchia |
| 6,241,729 B1 | 6/2001 | Estes |
| 6,280,442 B1 | 8/2001 | Barker |
| 6,296,609 B1 | 10/2001 | Brau |
| 6,319,257 B1 | 11/2001 | Carignan et al. |
| 6,322,500 B1 | 12/2001 | Ellefson |
| 6,340,345 B1 | 1/2002 | Lees |
| 6,416,465 B2 | 7/2002 | Brau |
| 6,447,443 B1 | 9/2002 | Keogh |
| 6,454,773 B1 | 9/2002 | Sherman |
| 6,478,800 B1 | 11/2002 | Fraser et al. |
| 6,506,151 B2 | 1/2003 | Estes |
| 6,524,238 B2 | 2/2003 | Velikaris |
| 6,551,242 B1 | 4/2003 | Furnish et al. |
| 6,559,240 B2 | 5/2003 | Hsu |
| 6,599,292 B1 | 7/2003 | Ray |
| 6,623,485 B2 | 9/2003 | Doubler |
| 6,632,238 B2 | 10/2003 | Ginn et al. |
| 6,660,004 B2 | 12/2003 | Barker |
| 6,675,805 B1 | 1/2004 | Graether |
| 6,689,054 B2 | 2/2004 | Furnish et al. |
| 6,692,434 B2 | 2/2004 | Ritland |
| 6,733,444 B2 | 5/2004 | Phillips |
| 6,749,613 B1 | 6/2004 | Conchy et al. |
| 6,802,844 B2 | 10/2004 | Ferree |
| 6,835,196 B2 | 12/2004 | Biedermann |
| 6,860,850 B2 | 3/2005 | Phillips |
| 6,869,398 B2 | 3/2005 | Obenchain et al. |
| 6,887,197 B2 | 5/2005 | Phillips |
| 6,887,198 B2 | 5/2005 | Phillips |
| 6,918,911 B2 | 7/2005 | Biedermann et al. |
| 6,929,606 B2 | 8/2005 | Ritland |
| 6,945,933 B2 | 9/2005 | Branch |
| 6,951,538 B2 | 10/2005 | Ritland |
| 6,964,666 B2 | 11/2005 | Jackson |
| 7,001,333 B2 | 2/2006 | Hamel |
| 7,011,658 B2 | 3/2006 | Young |
| 7,014,608 B2 | 3/2006 | Larson |
| 7,029,472 B1 | 4/2006 | Fortin |
| 7,108,698 B2 | 9/2006 | Robbins |
| 7,147,599 B2 | 12/2006 | Phillips |
| 7,150,714 B2 | 12/2006 | Myles |
| 7,166,073 B2 | 1/2007 | Ritland |
| 7,182,729 B2 | 2/2007 | Abdelgany |
| 7,207,949 B2 | 4/2007 | Miles |
| 7,214,186 B2 | 5/2007 | Ritland |
| 7,235,048 B2 | 6/2007 | Rein |
| 7,250,052 B2 | 7/2007 | Landry et al. |
| 7,318,817 B2 | 1/2008 | Hamada |
| 7,374,534 B2 | 5/2008 | Dalton |
| 7,396,328 B2 | 7/2008 | Penenberg |
| 7,455,639 B2 | 11/2008 | Ritland |
| 7,473,223 B2 | 1/2009 | Fetzer |
| 7,537,565 B2 | 5/2009 | Bass |
| 7,569,014 B2 | 8/2009 | Bass |
| 7,582,058 B1 | 9/2009 | Miles |
| 7,588,537 B2 | 9/2009 | Bass |
| 7,588,593 B2 | 9/2009 | Aferzon |
| 7,654,954 B1 | 2/2010 | Phillips |
| 7,686,809 B2 | 3/2010 | Triplett et al. |
| 7,691,057 B2 | 4/2010 | Miles |
| 7,722,618 B2 | 5/2010 | Estes |
| 7,753,844 B2 | 7/2010 | Sharratt |
| 7,758,501 B2 | 7/2010 | Frasier |
| 7,819,801 B2 | 10/2010 | Miles |
| 7,850,608 B2 | 12/2010 | Hamada |
| 7,892,173 B2 | 2/2011 | Miles et al. |
| 7,905,840 B2 | 3/2011 | Pimenta |
| 7,909,829 B2 | 3/2011 | Patel |
| 7,909,848 B2 | 3/2011 | Patel |
| 7,918,792 B2 | 4/2011 | Drzyzga et al. |
| 7,922,658 B2 | 4/2011 | Cohen |
| 7,927,337 B2 | 4/2011 | Keller |
| 7,931,589 B2 | 4/2011 | Cohen |
| 7,935,051 B2 | 5/2011 | Miles et al. |
| 7,935,053 B2 | 5/2011 | Karpowicz |
| 7,946,982 B2 | 5/2011 | Hamada |
| 7,959,564 B2 | 6/2011 | Ritland |
| 7,981,031 B2 | 7/2011 | Frasier |
| 8,043,343 B2 | 10/2011 | Miller et al. |
| 8,062,217 B2 | 11/2011 | Boucher |
| 8,066,710 B2 | 11/2011 | Estes |
| 8,100,828 B2 | 1/2012 | Frey et al. |
| 8,137,284 B2 | 3/2012 | Miles |
| 8,167,887 B2 | 5/2012 | McLean |
| 8,182,423 B2 | 5/2012 | Miles et al. |
| 8,187,179 B2 | 5/2012 | Miles et al. |
| 8,192,356 B2 | 6/2012 | Miles et al. |
| 8,192,357 B2 | 6/2012 | Miles et al. |
| 2002/0161368 A1 | 10/2002 | Foley et al. |
| 2003/0149341 A1 | 8/2003 | Clifton |
| 2004/0068269 A1 | 4/2004 | Bonati et al. |
| 2004/0147936 A1 | 7/2004 | Rosenberg et al. |
| 2004/0215199 A1 | 10/2004 | Zinkel |
| 2004/0230191 A1 | 11/2004 | Frey |
| 2005/0021031 A1 | 1/2005 | Foley et al. |
| 2005/0080320 A1 | 4/2005 | Lee et al. |
| 2005/0090824 A1 | 4/2005 | Shluzas et al. |
| 2005/0131422 A1 | 6/2005 | Anderson et al. |
| 2005/0148826 A1 | 7/2005 | Paolitto et al. |
| 2005/0165408 A1 | 7/2005 | Puno et al. |
| 2005/0171542 A1 | 8/2005 | Biedermann |
| 2005/0192486 A1 | 9/2005 | Harnel |
| 2005/0192570 A1 | 9/2005 | Jackson |
| 2005/0234304 A1 | 10/2005 | Dewey |
| 2005/0240081 A1 | 10/2005 | Eliachar |
| 2005/0245928 A1 | 11/2005 | Colleran et al. |
| 2005/0277812 A1 | 12/2005 | Myles |
| 2005/0277928 A1 | 12/2005 | Boschert |
| 2006/0025771 A1 | 2/2006 | Jackson |
| 2006/0036244 A1 | 2/2006 | Spitler |
| 2006/0100622 A1 | 5/2006 | Jackson |
| 2006/0111712 A1 | 5/2006 | Jackson |
| 2006/0111715 A1 | 5/2006 | Jackson |
| 2006/0142761 A1 | 6/2006 | Landry |
| 2006/0149232 A1 | 7/2006 | Sasing |
| 2006/0149240 A1 | 7/2006 | Jackson |
| 2006/0183978 A1 | 8/2006 | Howard |
| 2006/0189848 A1 | 8/2006 | Penenberg |

(56) References Cited

U.S. PATENT DOCUMENTS

| | | |
|---|---|---|
| 2006/0200133 A1 | 9/2006 | Jackson |
| 2006/0206009 A1 | 9/2006 | Von Wald |
| 2006/0241603 A1 | 10/2006 | Jackson |
| 2006/0241618 A1 | 10/2006 | Gasser |
| 2006/0247637 A1 | 11/2006 | Colleran |
| 2006/0247658 A1 | 11/2006 | Pond |
| 2006/0271047 A1 | 11/2006 | Jackson |
| 2006/0271050 A1 | 11/2006 | Piza Vallespir |
| 2006/0276789 A1 | 12/2006 | Jackson |
| 2006/0276792 A1 | 12/2006 | Ensign |
| 2006/0287674 A1 | 12/2006 | Ginn et al. |
| 2007/0016200 A1 | 1/2007 | Jackson |
| 2007/0038033 A1 | 2/2007 | Jones |
| 2007/0049931 A1 | 3/2007 | Justis |
| 2007/0049933 A1 | 3/2007 | Ahn |
| 2007/0055240 A1 | 3/2007 | Matthis |
| 2007/0055241 A1 | 3/2007 | Matthis |
| 2007/0055244 A1 | 3/2007 | Jackson |
| 2007/0073111 A1 | 3/2007 | Bass |
| 2007/0073112 A1 | 3/2007 | Holmes |
| 2007/0083086 A1 | 4/2007 | LeVahn |
| 2007/0088357 A1 | 4/2007 | Johnson |
| 2007/0090238 A1 | 4/2007 | Justis |
| 2007/0093818 A1 | 4/2007 | Biedermann |
| 2007/0093828 A1 | 4/2007 | Abdou |
| 2007/0100212 A1 | 5/2007 | Pimenta |
| 2007/0106123 A1 | 5/2007 | Gorek et al. |
| 2007/0123862 A1 | 5/2007 | Warnick |
| 2007/0123870 A1 | 5/2007 | Jeon et al. |
| 2007/0129608 A1 | 6/2007 | Sandhu |
| 2007/0135817 A1 | 6/2007 | Ensign |
| 2007/0167949 A1 | 7/2007 | Altarac et al. |
| 2007/0173819 A1 | 7/2007 | Sandlin |
| 2007/0179343 A1 | 8/2007 | Shelokov |
| 2007/0191955 A1 | 8/2007 | Zucherman et al. |
| 2007/0198062 A1 | 8/2007 | Miles et al. |
| 2007/0208227 A1 | 9/2007 | Smith et al. |
| 2007/0208228 A1 | 9/2007 | Pavento et al. |
| 2007/0225568 A1 | 9/2007 | Colleran |
| 2007/0233079 A1 | 10/2007 | Fallin et al. |
| 2007/0233097 A1 | 10/2007 | Anderson et al. |
| 2007/0238932 A1 | 10/2007 | Jones et al. |
| 2007/0270842 A1 | 11/2007 | Bankoski et al. |
| 2008/0021285 A1 | 1/2008 | Drzyzga |
| 2008/0058606 A1 | 3/2008 | Miles et al. |
| 2008/0077136 A1 | 3/2008 | Triplett |
| 2008/0077138 A1 | 3/2008 | Cohen |
| 2008/0114208 A1 | 5/2008 | Hutton |
| 2008/0146881 A1 | 6/2008 | Alimi |
| 2008/0183044 A1 | 7/2008 | Colleran |
| 2008/0183046 A1 | 7/2008 | Boucher et al. |
| 2008/0188718 A1 | 8/2008 | Spitler |
| 2008/0249372 A1 | 10/2008 | Reglos |
| 2008/0262318 A1 | 10/2008 | Gorek |
| 2009/0012370 A1 | 1/2009 | Gutierrez |
| 2009/0018399 A1 | 1/2009 | Martinelli et al. |
| 2009/0036746 A1 | 2/2009 | Blackwell et al. |
| 2009/0076333 A1 | 3/2009 | Bjork |
| 2009/0076516 A1 | 3/2009 | Lowry |
| 2009/0105547 A1 | 4/2009 | Vayser |
| 2009/0124861 A1 | 5/2009 | Fetzer |
| 2009/0222046 A1 | 9/2009 | Gorek |
| 2009/0227845 A1 | 9/2009 | Lo et al. |
| 2010/0030224 A1 | 2/2010 | Winslow et al. |
| 2010/0081885 A1 | 4/2010 | Wing |
| 2010/0114182 A1 | 5/2010 | Wilcox et al. |
| 2010/0137915 A1 | 6/2010 | Anderson et al. |
| 2010/0217089 A1 | 8/2010 | Farley |
| 2010/0249856 A1 | 9/2010 | Lott et al. |
| 2010/0298647 A1 | 11/2010 | Black |
| 2010/0298648 A1 | 11/2010 | Gray |
| 2010/0312068 A1 | 12/2010 | Dalton |
| 2010/0331901 A1 | 12/2010 | Lott et al. |
| 2011/0004067 A1 | 1/2011 | Marchek |
| 2011/0022088 A1 | 1/2011 | Forton et al. |
| 2011/0034780 A1 | 2/2011 | Loftus et al. |
| 2011/0034781 A1 | 2/2011 | Loftus et al. |
| 2011/0130793 A1* | 6/2011 | Woolley et al. ............... 606/279 |
| 2011/0137130 A1 | 6/2011 | Thalgott |
| 2011/0201897 A1 | 8/2011 | Bertagnoli |
| 2011/0208008 A1 | 8/2011 | Michaeli |
| 2011/0224497 A1 | 9/2011 | Weiman |
| 2011/0245836 A1 | 10/2011 | Hamada |
| 2011/0257487 A1 | 10/2011 | Thalgott |
| 2011/0301423 A1 | 12/2011 | Koros |
| 2012/0065693 A1 | 3/2012 | Lim et al. |

FOREIGN PATENT DOCUMENTS

| | | |
|---|---|---|
| FR | 2788958 | 8/2000 |
| JP | 10277043 | 10/1998 |
| WO | 98/38921 | 9/1998 |
| WO | 01/06940 | 2/2001 |
| WO | 2008/082836 | 7/2008 |
| WO | 2008/131084 | 10/2008 |
| WO | 2010/057980 | 5/2010 |

OTHER PUBLICATIONS

Dhall et al., "Clinical and Radiographic comparison of Mini-open Transforaminal Lumbar Interbody Fusion With Open Transforaminal Lumbar Interbody Fusion in 42 Patients with Long Term Follow-up," *J. Neurosurg Spine*, 2008, 9: 560-565.

Foley et al, "Minimally Invasive Lumbar Fusion," *Spine*, 2003, 28:S26-S35.

Holly et al., "Minimally Invasive Transformainal Lumbar Interbody Fusion: indications, technique, and Complications," *Neurosurg Focus*, 2006, 20:E6, 5 pages.

Mummaneni and Rodts, "The mini-open transforminal Lumbar Interbody Fusion," *Neurosurgery*, 2005, S7: 256-261.

Ozgur et al., "Minimally Disruptive Decompression and Transforaminal Lumbar Interbody Fusion," *The Spine Journal*, 2006, 6: 27-33.

Ozgur et al., "Minimally-invasive Technique for Transforaminal Lumbar Interbody Fusion (TLIF)," *Eur Spine J*, 2005, 14: 887-894.

Schwender et al., "Minimally invasive transforaminal lumbar interbody fusion (TLIF): technical feasibility and initial results," *J Spinal Disord Tech*. 2005, 18(1):S1-S6.

* cited by examiner

TISSUE RETRACTION SYSTEM AND RELATED METHODS

CROSS-REFERENCE TO RELATED APPLICATIONS

This application is a non-provisional patent application claiming the benefit of priority from U.S. Provisional Patent Application Ser. No. 61/296,468, filed on Jan. 19, 2010, the entire contents of which is hereby expressly incorporated by reference into this disclosure as if set forth in its entirety herein.

FIELD

The present invention relates to implants and methods generally aimed at surgery and, more particularly, to improved systems and methods for performing spine surgery.

BACKGROUND

Spinal discs serve to cushion and stabilize the spine in addition to distributing stress and damping cyclic loads. The discs may become damaged due to injury or age and symptoms of a damaged disc may include severe pain, numbness or muscle weakness. Fusion is one method of reducing the magnitude of the symptoms of damaged spinal discs. The primary goals of fusion procedures are to provide stability between the vertebrae on either side of the damaged disc and to promote natural fusion of those adjacent vertebrae.

In a typical spinal fusion surgery, for example, a tissue retractor is used to create and maintain an operative corridor through a patient's skin to a target disc space. This retractor is secured to the operating table via an articulating arm. However, this arrangement can have disadvantages in that the retractor is registered to the table, and thus any movement of the patient (however slight) may shift the operative corridor slightly. This can create a delay in the surgical procedure as the surgeon must reestablish the proper operative corridor by repositioning the patient, often requiring additional fluoroscopy usage that wouldn't otherwise be necessary in order to verify positioning. Furthermore, even if the slight shift of the operative corridor does not require repositioning of the patient, often times there will be tissue creep into the operative corridor due to the split-blade nature of the retractor. Also, slight movement of the operative corridor may cause other anatomical interference with the retractor blades, such as ribs in a thoracic spine example, or the iliac crest in a lumbar spine example. Also, fixation to the spine creates a truly rigid fixation system. The present invention is directed at addressing the shortcomings of the prior art.

SUMMARY OF THE INVENTION

The present invention accomplishes this goal by providing a tissue retraction system including attachment shims that securely and rigidly attach distal ends of the retractor blades to bone screws implanted in a patient. Thus, the retractor is registered to the patient rather than the operating table. Such a configuration ensures that the operative corridor does not shift relative to the patient at any time. This has the advantage of minimizing tissue creep into the operative corridor, and also removes the potential of anatomical interference since the location of nearby spinal anatomy does not change relative to the operative corridor, once established. Thus, small shifts in patient positioning are not problematic. Also, the present invention allows distraction, compression, and deformity correction.

To accomplish this goal, a tissue retraction system is provided including a tissue retractor having a body and a plurality of retractor blades. Attachment shims are also provided to enable secure, rigid attachment of the retractor blades to implanted bone screws. The attachment shims are configured to slideably engage the retractor blades to enable easy introduction into the surgical target site. By way of example only, the attachment shims may have an elongated body with an engagement member at its distal end. In one embodiment, the engagement member includes a ring member having a gap formed therein. The gap allows passage of the one screw therethrough. The gap may be slightly smaller than the portion of the bone screw that traverses the gap, thereby requiring the ring member to slightly flex to allow passage of the bone screw. This enables a "snap-fit" engagement between the shim and the screw.

Several alternative configurations of the attachment shim are possible without departing from the scope of the present invention. According to one embodiment, the ring member may include a 270° arc between the base of the shim and the gap. According to another embodiment, the ring member may include a generally C-shaped clamp mechanism. According to another embodiment, the ring member may be offset from the retractor blade via an extension. According to yet another embodiment, the, engagement member may comprise a locking bar with a set screw. Cannulated screws may be utilized—placed over K-wires inserted into the bone on either side of the disc.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The tissue retraction system disclosed herein boasts a variety of inventive features and components that warrant patent protection, both individually and in combination.

Figure 1:
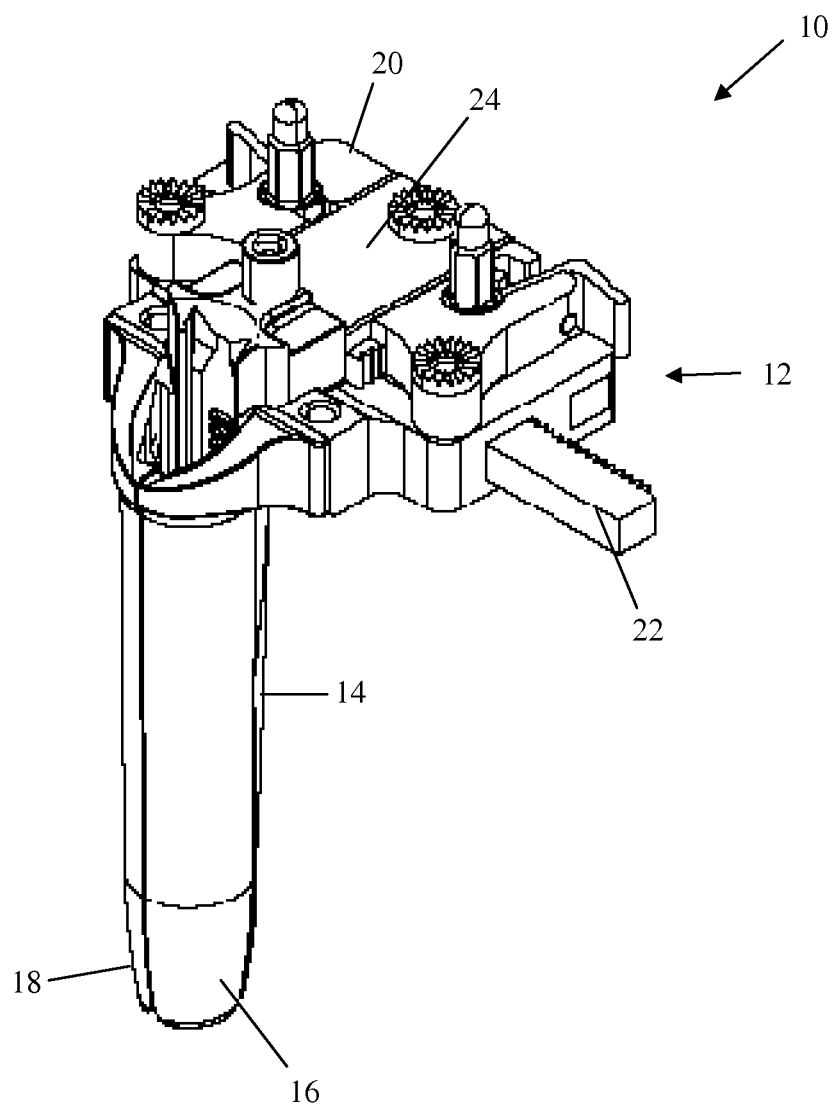
FIG. 1 is a perspective view of an example of a tissue retraction assembly capable of being used with the present invention, shown in an initial "closed" position.
Figure 2:
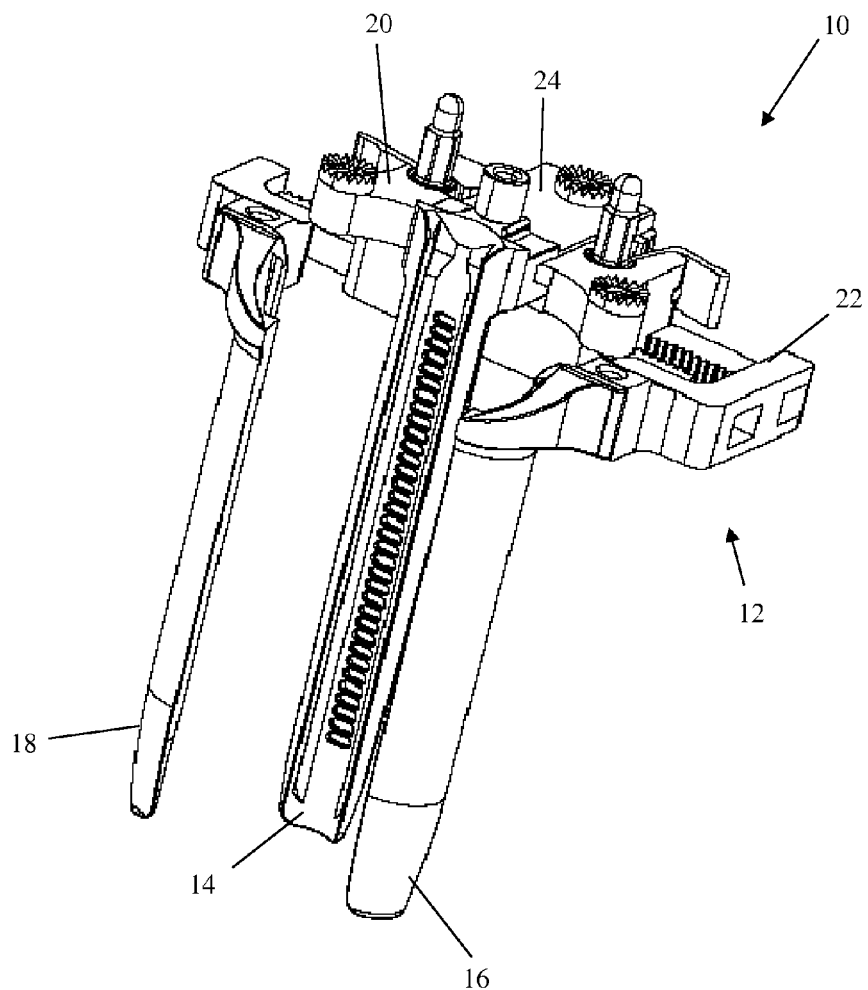
FIGS. 2-3 are perspective and top plan views, respectively, of the tissue retraction assembly of FIG. 1, shown in a secondary "open" position.
Figure 3:
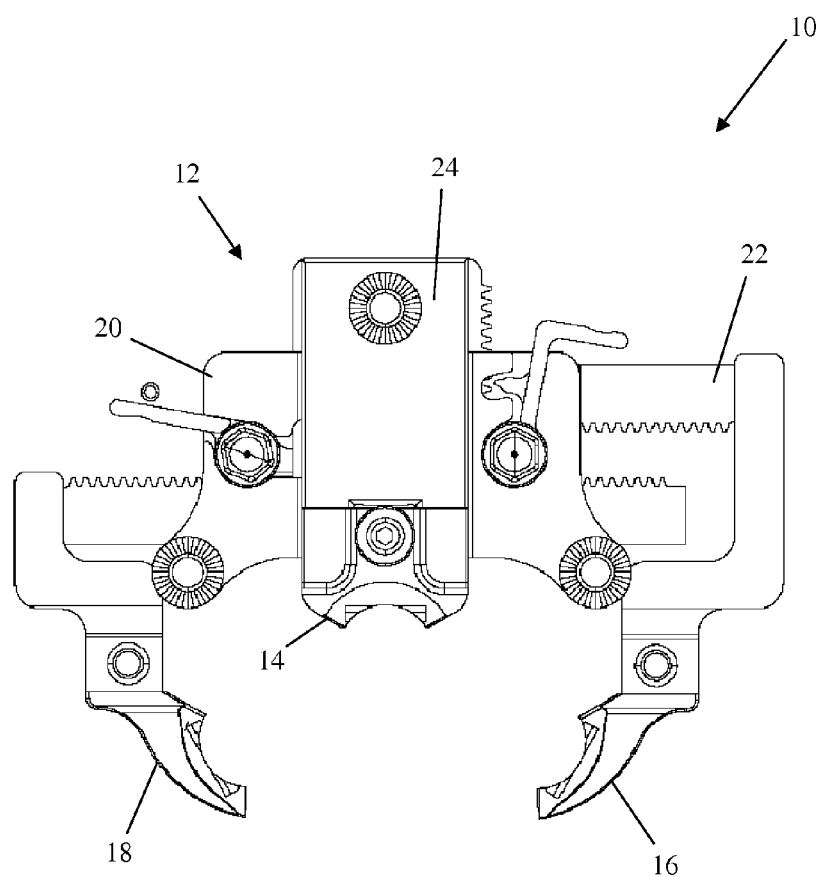

FIGS. 1-3 illustrate an example of a tissue retraction assembly 10 configured for use with the attachment shim of the present invention. By way of example only, the tissue retraction assembly 10 is similar to one disclosed in U.S. Provisional Patent Application No. 61/105,791, filed Oct. 15, 2008 and entitled "Systems and Methods for Performing Spinal Fusion Surgery," the contents of which are incorporated herein by reference with no claim of inventorship. The tissue retraction assembly 10 is configured to establish an operative corridor through a patient's skin to a surgical target site. By way of example only, the surgical target site may be an intervertebral disc located between adjacent vertebral bodies of a human spine. Although described for use in this fashion, the tissue retraction system described herein may be used with any part of the body without departing from the scope of the present invention. Prior to using the retractor, an initial distraction assembly (not shown) may be used to establish an initial distraction corridor. For example, this initial distraction assembly may include a K-wire and sequential dilator kit of the kind commonly used in the art. The tissue retraction assembly 10 is configured to slideably engage the tissue distraction assembly in initial "closed" configuration (as shown in FIG. 1), and thereafter be moved to a second "open" position (as shown in FIGS. 2-3) to establish and maintain the operative corridor (or working channel). According to one broad aspect of the present invention, the tissue retraction assembly 10 includes a retractor body 12 and a plurality of retractor blades 14, 16, 18. Retractor blades 14, 16, 18 may be provided in any size and shape suitable to establish and maintain an operative corridor to the surgical target site. For example, the retractor assembly 10 is shown in a "closed" position in FIG. 1, wherein the initial "closed" position has a generally circular cross-section. However, a plurality of retractor blades may be provided having an initial "closed" position having a generally oblong cross-section without departing from the scope of the present invention.

In the example shown, the retractor body portion 12 includes a housing member 20, a rack member 22, and a medial retraction member 24. Broadly, the housing member 20 provides a scaffold to hold the various components together. The rack member 22 is dimensioned to provide a mechanism to expand the retractor blades 16, 18 in a first (e.g. caudal-cranial) direction. The medial retraction member 24 provides a mechanism to expand the retractor blade 14 in a second (e.g. medial) direction.

Figure 4:
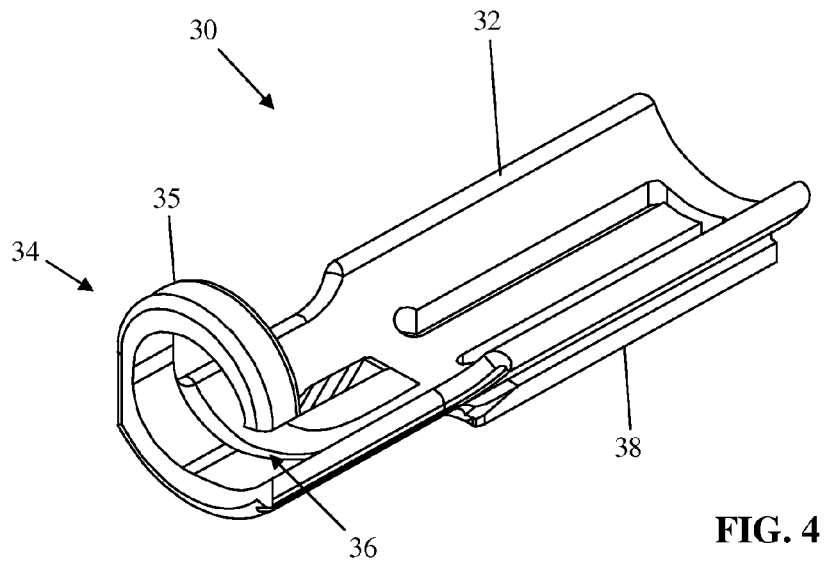
FIGS. 4-5 are perspective views of an example of an attachment shim for use with the tissue retraction assembly of FIG. 1, according to one embodiment of the present invention.
Figure 5:
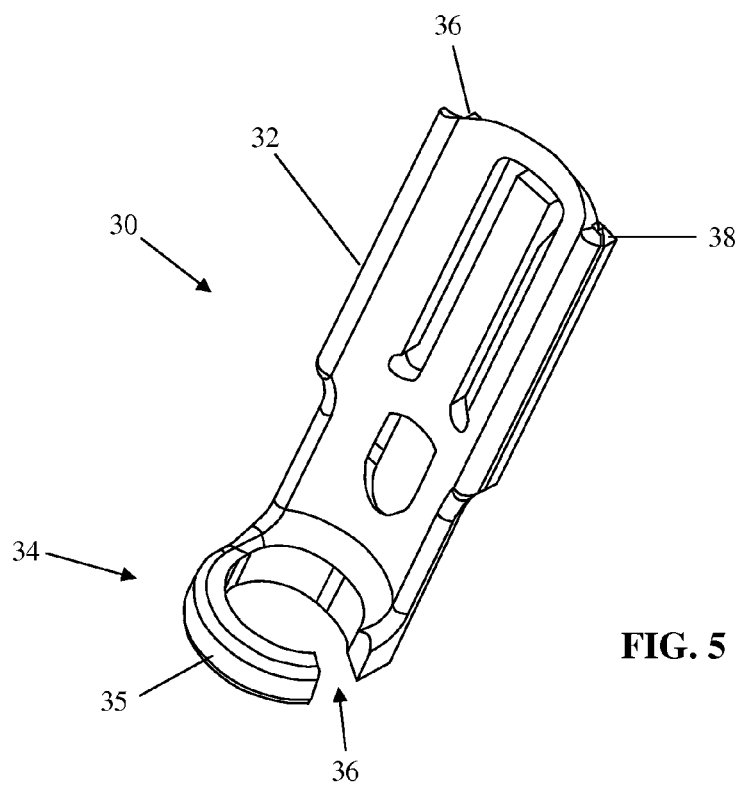

FIGS. 4-5 illustrate an example of an attachment shim 30 according to one embodiment of the present invention. Attachment shim 30 is dimensioned to provide temporary but secure and rigid attachment of the retractor blades 16, 18 to a bone screw inserted into the surgical target site. Attachment shim 30 includes an elongated body 32 and an engagement member 34 positioned distally on the shim 30. By way of example, the engagement member 34 of the attachment shim 30 of this embodiment is in the form of a broken ring having an opening or gap 36 positioned therein. The gap 36 is dimensioned to allow the passage of at least a portion of a bone screw therethrough. By way of example only, the gap 36 may be large enough to allow passage of a shank portion of a bone screw, such that the engagement member may be side loaded onto the shank below the head of the bone screw (which may or may not be mated with a rod receiving tulip portion—not shown). The gap 36 may be provided with a dimension slightly smaller than a passable portion of a bone screw, such that the ring 35 is required to flex or deform slightly to allow passage of the portion of the bone screw, then snap back into place once the bone screw has passed through the gap. Such a dimension of the gap 36 creates a "snap-fit" relationship between the attachment shim 30 and the bone screw.

Figure 10:
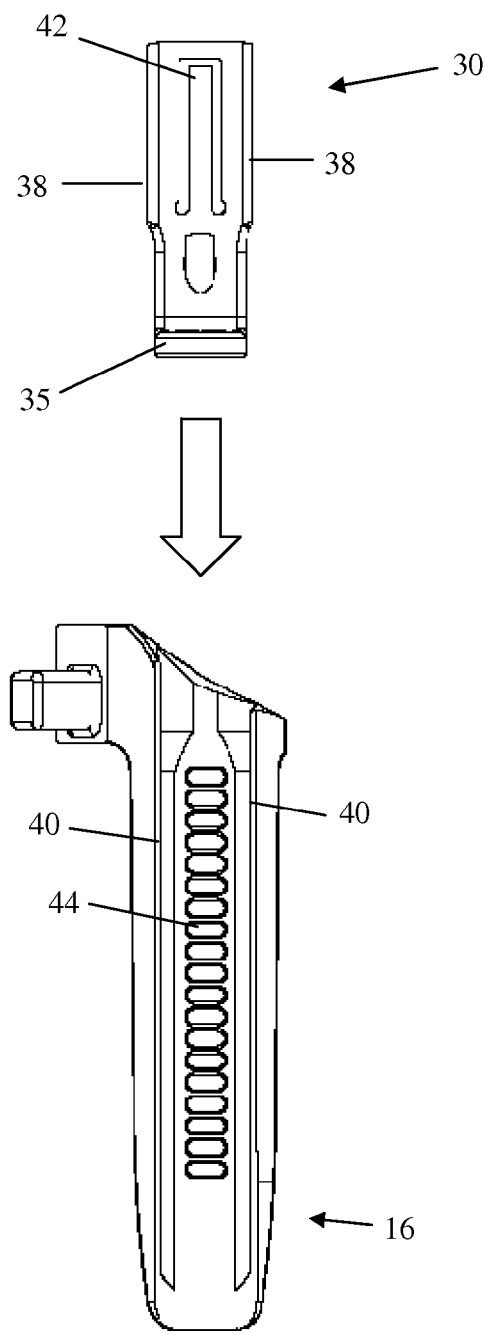
FIG. 10 is a plan view of a step in engaging the attachment shim of FIG. 4 with a retractor blade forming part of the tissue retraction assembly of FIG. 1.

The attachment shim 30 further includes attachment features 38 that enable the shim to be slideably advanced along the retractor blades 16, 18. Attachment features 38 are wing-like extensions that engage the tracks 40 on the retractor blade 16, 18 (FIG. 10). Optionally, attachment shim 30 may further include a control element 42 comprising a deflectable portion that interacts with a plurality of recesses 44 provided on the retractor blades 16, 18 (FIG. 10). This feature is provided to allow the shim to be controllably advanced to the surgical target site.

Figure 6:
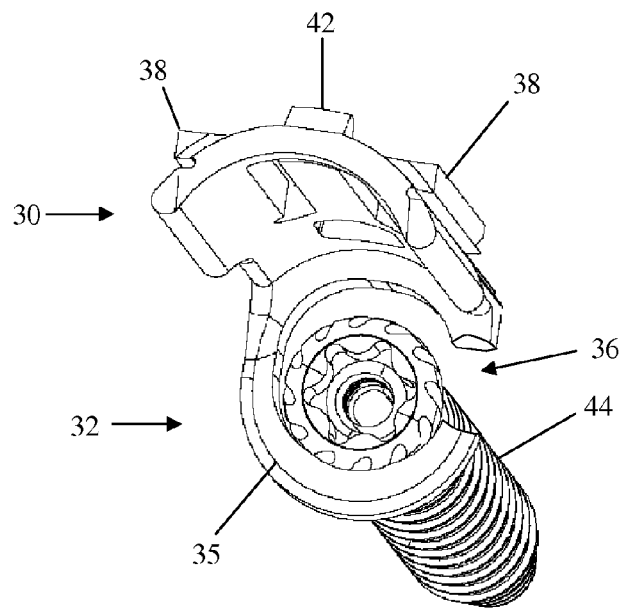
FIG. 6 is a perspective view of the attachment shim of FIG. 4 engaged with an example of a bone screw.

FIG. 6 illustrates the attachment shim 30 in engagement with an example of a bone screw 44. The attachment member 32 fits over the head of the bone screw 44 to allow for secure interaction between the attachment member 32 and bone screw 44. This interaction between the attachment member 34 and bone screw 44 is important because it provides a temporary but secure attachment for the retractor blades to help keep the operative corridor secure during the surgical procedure, enabling the retractor to be secured to the patient (via the screws) rather than the hospital bed (via an articulating arm). Thus, if the patient were to be moved slightly in any direction, the retractor would move with the patient, and the operative corridor would not change at all since the retractor is secured at the screws.

Figure 7:
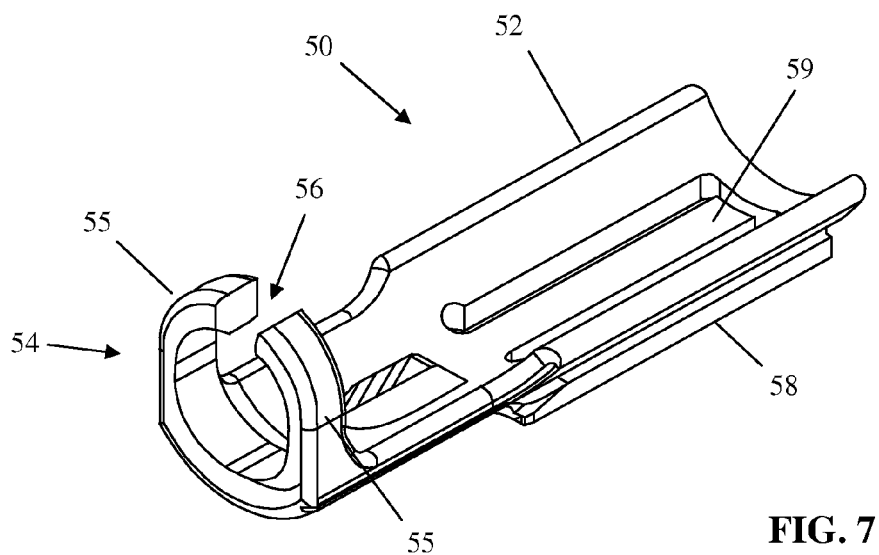
FIG. 7 is a perspective view of an example of an attachment shim according to an alternative embodiment of the present invention.

As shown by way of example in FIGS. 4-6, the gap 36 is positioned on one side of the ring 35 near the base of the shim 30. However, other configurations are possible. For example, FIG. 7 illustrates an example of an attachment shim 50 according to an alternative embodiment of the present invention. Attachment shim 50 is like attachment shim 30 except for the orientation of the ring portion 55. Attachment shim 50 includes an elongated body 52 and an engagement member 54 positioned distally on the shim 50. By way of example, the engagement member 54 of the attachment shim 50 of this embodiment is in the form of a broken ring 55 having an opening or gap 56 positioned therein. In the embodiment of FIG. 7, the gap 56 is positioned within the ring 55 opposite the base of the shim 50, in a generally C-shaped configuration. The attachment shim 50 further includes attachment features 58 that enable the shim to be slideably advanced along the retractor blades 16, 18. Attachment features 58 are wing-like extensions that engage the tracks 40 on the retractor blade 16, 18 (FIG. 10). Optionally, attachment shim 50 may further include a control element 59 comprising a deflectable portion that interacts with a plurality of recesses 44 provided on the retractor blades 16, 18 (FIG. 10).

Figure 8:
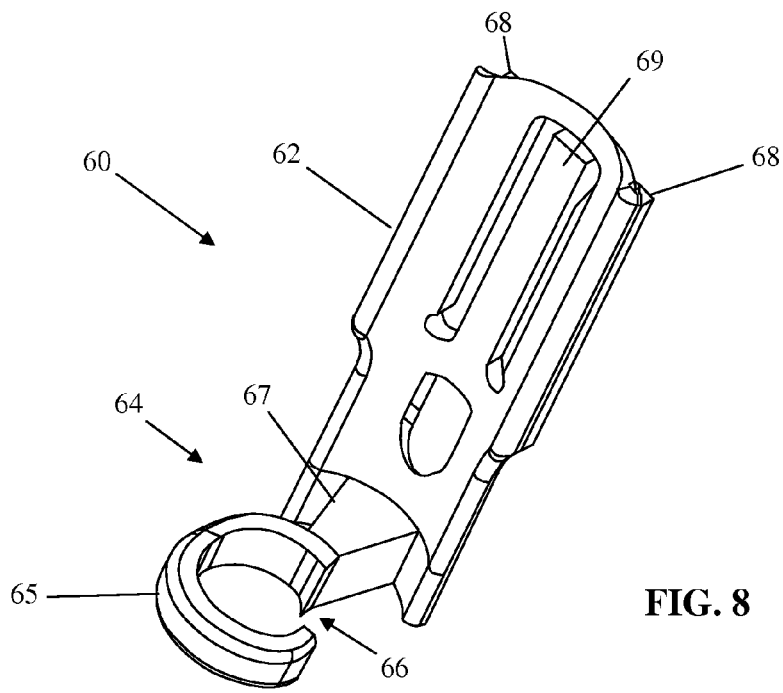
FIG. 8 is a perspective view of an example of an attachment shim according to an another embodiment of the present invention.

FIG. 8 illustrates an example of an attachment shim 60 according to another alternative embodiment of the present invention. Attachment shim 60 is like attachment shims 30 except for the orientation of the ring portion 65. Attachment shim 60 includes an elongated body 62 and an engagement member 64 positioned distally on the shim 60. By way of example, the engagement member 64 of the attachment shim 60 of this embodiment is in the form of a broken ring 65 having an opening or gap 66 positioned therein. In the embodiment of FIG. 8, the ring 65 is oriented in an approximate 270° arc that is separated from the base of the shim 60 by an extension 67. The attachment shim 60 further includes attachment features 68 that enable the shim to be slideably advanced along the retractor blades 16, 18. Attachment features 68 are wing-like extensions that engage the tracks 40 on the retractor blade 16, 18 (FIG. 10). Optionally, attachment shim 60 may further include a control element 69 comprising a deflectable portion that interacts with a plurality of recesses 44 provided on the retractor blades 16, 18 (FIG. 10).

Figure 9:
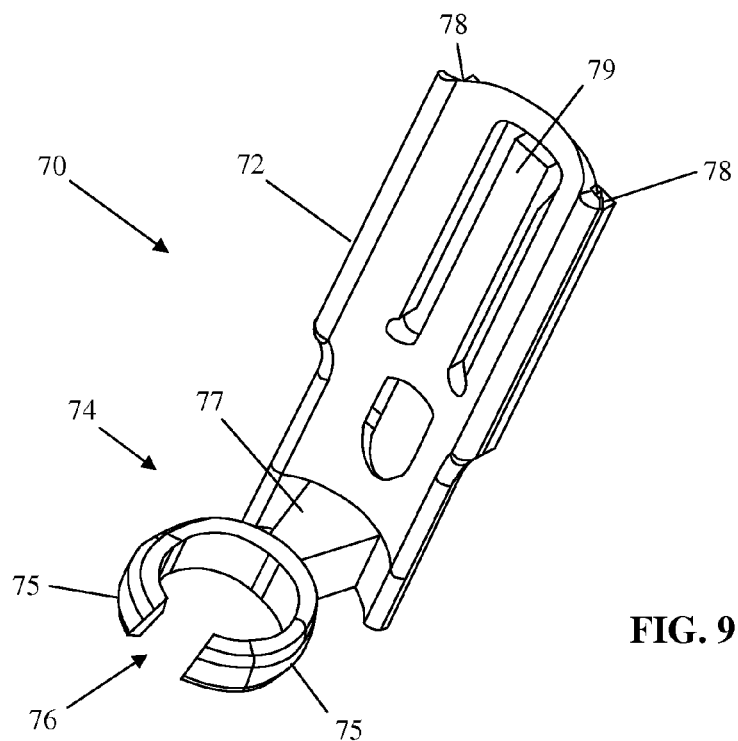
FIG. 9 is a perspective view of an example of an attachment shim according to an another embodiment of the present invention.

FIG. 9 illustrates an example of an attachment shim 70 according to yet another alternative embodiment of the present invention. Attachment shim 70 is like attachment shim 50 except for the orientation of the ring portion 75. Attachment shim 70 includes an elongated body 72 and an engagement member 74 positioned distally on the shim 70. By way of example, the engagement member 74 of the attachment shim 70 of this embodiment is in the form of a broken ring 75 having an opening or gap 76 positioned therein. In the embodiment of FIG. 9, the gap 76 is positioned within the ring 75 opposite the base of the shim 70, in a generally C-shaped configuration that is separated from the base of the shim 70 by an extension 77. The attachment shim 70 further includes attachment features 78 that enable the shim to be slideably advanced along the retractor blades 16, 18. Attachment features 78 are wing-like extensions that engage the tracks 40 on the retractor blade 16, 18 (FIG. 10). Optionally, attachment shim 70 may further include a control element 79 comprising a deflectable portion that interacts with a plurality of recesses 44 provided on the retractor blades 16, 18 (FIG. 10).

According to another embodiment, the engagement member may comprise a locking bar with set screw (not shown). This configuration can be advantageous in situations where the implanted bone screw includes a tulip portion. The locking bar is received within the tulip, and a set screw is employed to lock the locking bar within the tulip.

FIG. 10 illustrates the step of coupling the attachment shim member 30 to the retractor blade 16. The shim 30 is coupled to the blade 16 by engaging the attachment features 38 of the shim 30 to the tracks 40 on the blade 16. The shim 30 is then advanced along the length of the blade 16 until it is at the distal end of the blade. The interaction between the control element 42 of the shim 30 and the recess 44 of the blade 16 prevent the shim 30 from migrating along the blade 16 during surgery. At this point, the shim 30 is ready to be engaged to the bone screw 44, as described above. The shim 30 is removable from the blade 16 with the use of an appropriate removal tool (not shown) configured to disengage the control element 42 from the recess and slideably remove the shim 30 from the blade 16.

To use the retractor 10 according to the method of the present invention, creation of the operative corridor may follow methodology of initial distraction and retraction commonly known in the art. For example, the first step is the placement of one or more K-wires through small incisions in the skin to the target surgical site. To assist with this, the surgeon may use navigated guidance system. At this point, an initial dilator is advanced over the K-wires toward the surgical target site. Next, a secondary dilator is advanced over the initial dilator to enlarge the distraction corridor. This secondary dilation step may be repeated with sequentially larger dilators until a desired size of the distraction corridor is reached.

Figure 11:
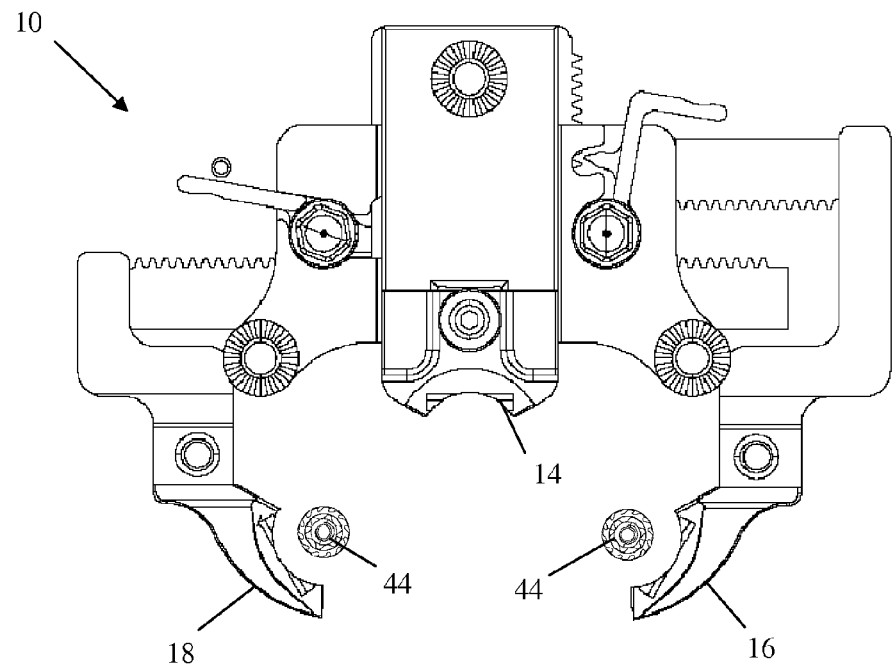
FIG. 11 is a top plan view of the tissue retraction assembly of FIG. 1 in an "open" position allowing access to a pair of implanted pedicle screws according to one embodiment of the present invention.

Once the distraction corridor is sized to the desire of the surgeon, retractor blades 14, 16, 18 (attached to the retractor 10) are advanced over the tissue distraction assembly. Once the blades have been inserted, the retractor may be (though not necessarily) secured in position relative to the hospital bed using an articulating arm. The tissue distraction assembly may be removed because the retractor blades are now maintaining the operative corridor. The operative corridor may now be expanded in the first direction (e.g. caudal and cephalad) by causing the retractor blades 16, 18 to move. At this point, the operative corridor may be retracted in the second direction (e.g. medially) if desired. Once the desired operative corridor is established, bone screws are driven into the bone. In the example provided herein, a pair of bone screws are inserted—a cranial screw and a caudal screw ("cranial" and "caudal" being used to describe the relative positioning within the surgical target site). Preferably, the caudal-most retractor blade 16 will be positioned caudally of the caudal bone screw 44, and the cranial-most retractor blade 18 will be positioned cranially of the cranial bone screw 44, thereby ensuring that the surgeon's entire operative field is included within the established operative corridor (as shown in FIG. 11).

Figure 12:
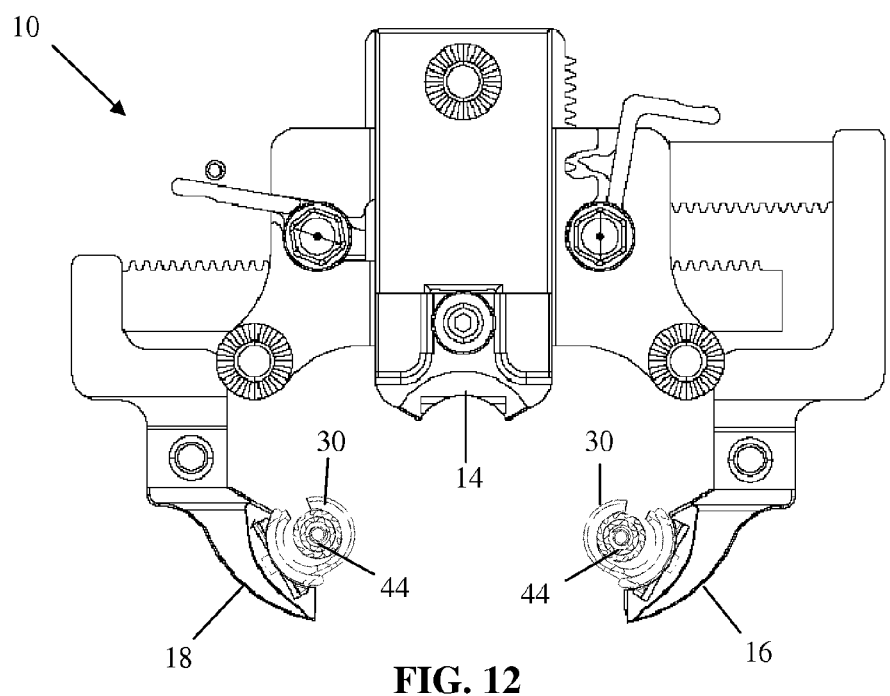
FIG. 12 is a top plan view of the tissue retraction assembly of FIG. 11 including attachment shims engaged with the bone screws according to one embodiment of the present invention.

As illustrated by FIG. 12, once the bone screws have been implanted successfully, attachment shims 30 may be employed to securely attach the caudal and cranial retractor blades to the respective bone screws. At this point, the retractor 10 is disconnected from the articulating arm, and the articulating arm may be removed from the surgical field. The retractor 10 is now securely attached to the bone screws implanted in the patient, and the operative corridor is established with respect to the patient. If the patient were to move in any way (e.g. slight bumping or rotating of the body), the established operative corridor would not change. The surgeon may now work on the disc space to perform the desired surgical technique. Rod receiving tulips may thereafter be connected to the bone screws (if not previously engaged) and a fixation rod fixed in position prior to removing the fixation shims (if desired) since the shims 30 are disengaged sideways from the bone screw 44 beneath the tulip.

Furthermore, if a fixation plate is desired, the plate may be attached to the bone screws (which may be provided in the form of bolts) without first removing the attachment shims 30. This is possible because the gap 36 enables the shim 30 to be disengaged from the bone screw 44 from underneath the plate.

An additional advantage of securing the retractor blades to the bone screws is that the retractor may be used to distract the disc space if desired. This may be done before or after the retractor has been detached from the articulating arm without departing from the scope of the present invention.

According to one embodiment, the retraction system of the present invention may be used in scoliosis treatment. For example, bone screws may be inserted in a desired spinal location (e.g. T10-L2 vertebral levels) according to the above described procedure. Preferably, the retractor 10 is inserted at the apex of a scoliosis curve. The retractor blades may then be secured to the bone screws and used to compress the area. Fixation rods (not shown) may then be advanced along the operative corridor and secured into position. The fulcrum of the retractor may thereafter aid in the reduction process.

Although described with respect to specific examples of the different embodiments, any features of the systems and methods disclosed herein by way of example only may be applied to any of the embodiments without departing from the scope of the present invention. Furthermore, procedures described for example only involving specific structure (e.g. vertebral bone) may be applied to another structure (e.g. femur) without departing from the scope of the present invention. Further, while this invention has been described in terms of a best mode for achieving this invention's objectives, it will be appreciated by those skilled in the art that variations may be accomplished in view of these teachings without deviating from the spirit or scope of the invention.

What is claimed is:

1. A surgical retraction system configured to provide rigid attachment to a plurality of bone anchors inserted into bone within a surgical target site, comprising:
    a retractor assembly having a plurality of blades advanceable to said surgical target site and opened to create an operative corridor to said surgical target site; and
    a plurality of attachment shims, each including an attachment ring that couples to a one of said plurality of bone anchors and a body that couples to one of said plurality of blades such that said retractor blades are locked in position relative to said bone anchors, said body being attached to said attachment ring along an attachment region that extends along a first portion of a circumference of the attachment ring, said attachment ring of each attachment shim having a side opening for passing said bone screw into said attachment ring, the side opening extending along a second portion of the circumference of the attachment ring that is separate from the first portion.

2. The system of claim 1, wherein said attachment ring comprises an arcuate member having 270° of curvature.

3. The system of claim 1, wherein said attachment ring comprises a generally C-shaped member configured to rigidly engage said bone anchor element.

4. The system of claim 1, where said attachment ring is attached to the attachment region by an extension.

5. The system of claim 1, wherein said side opening in said attachment ring is dimensioned to provide a snap-fit engagement with said bone anchor.

6. The system of claim 1, wherein said side opening is situated adjacent the attachment region.

7. The system of claim 1, wherein said side opening is situated opposite the attachment region.

* * * * *